(12) United States Patent
Lee

(10) Patent No.: US 11,213,239 B2
(45) Date of Patent: Jan. 4, 2022

(54) PORTABLE MULTI-LEAD ELECTROCARDIOGRAM DEVICE WITH INCLINED LEFT AND RIGHT HAND CONTACTS

(71) Applicant: VIE LONGUE BIOTECH INC., New Taipei (TW)

(72) Inventor: Chung-Liang Lee, New Taipei (TW)

(73) Assignee: VIE LONGUE BIOTECH INC., New Taipei (TW)

( * ) Notice: Subject to any disclaimer, the term of this patent is extended or adjusted under 35 U.S.C. 154(b) by 196 days.

(21) Appl. No.: 16/584,410

(22) Filed: Sep. 26, 2019

(65) Prior Publication Data

US 2021/0093212 A1 Apr. 1, 2021

(51) Int. Cl.
*A61B 5/332* (2021.01)
*A61B 5/00* (2006.01)
*A61B 5/282* (2021.01)
*A61B 5/06* (2006.01)

(52) U.S. Cl.
CPC .............. *A61B 5/332* (2021.01); *A61B 5/068* (2013.01); *A61B 5/282* (2021.01); *A61B 5/6823* (2013.01); *A61B 5/6826* (2013.01); *A61B 5/6887* (2013.01); *A61B 5/70* (2013.01)

(58) Field of Classification Search
None
See application file for complete search history.

(56) References Cited

U.S. PATENT DOCUMENTS

| | | | | |
|---|---|---|---|---|
| 5,191,891 A | * | 3/1993 | Righter | A61B 5/335 600/523 |
| 10,433,745 B1 | * | 10/2019 | Amitai | A61B 5/332 |
| 2005/0027203 A1 | * | 2/2005 | Umeda | A61B 5/332 600/509 |
| 2009/0112112 A1 | * | 4/2009 | Lee | A61B 5/443 600/523 |
| 2009/0299206 A1 | * | 12/2009 | Wang | A61B 5/332 600/522 |
| 2011/0015496 A1 | | 1/2011 | Sherman et al. | |
| 2015/0018660 A1 | * | 1/2015 | Thomson | A61B 5/332 600/393 |
| 2017/0143221 A1 | | 5/2017 | Shinozaki et al. | |
| 2021/0219902 A1 | * | 7/2021 | Vajdic | G16H 40/67 |

OTHER PUBLICATIONS

The extended European search report for 19200976.9, dated Mar. 25, 2020, Total of 7 pages.

* cited by examiner

*Primary Examiner* — Kennedy Schaetzle

(74) *Attorney, Agent, or Firm* — R. Lynette Wylie; Apex Juris, pllc.

(57) ABSTRACT

A portable multi-lead electrocardiogram device includes a holding case, a signal processing module and three metal contacts. The signal processing module is located in the holding case. The metal contacts are located on an exterior surface of the holding case and are electrically connected to the signal processing module. The metal contacts are respectively a body contact, a left hand contact and a right hand contact. The device can measure the electrical activities of the heart beat from two different directions, which greatly improves detecting capability. Professional 12-lead electrocardiogram can also be performed by multiple times of measuring. This portable device allows patients with history of myocardial infarction to perform electrocardiogram test timely when feeling ill and to seek medical attention early.

7 Claims, 6 Drawing Sheets

PORTABLE MULTI-LEAD ELECTROCARDIOGRAM DEVICE WITH INCLINED LEFT AND RIGHT HAND CONTACTS

BACKGROUND OF THE INVENTION

1. Field of the Invention

The present invention relates to a medical detection device, especially to an electrocardiogram device that is light and portable.

2. Description of the Prior Arts

When a heart beats, the nerve system located in various portions of the heart, such as the atrium and the ventricle, produces electrical impulses that cause the muscle of the heart to contract regularly. The electrical signal is transmitted to the skin surface of a human body, which generates small electrical potential changes on the skin. The condition of the heartbeat can be monitored by measuring the small electrical changes on the skin surface, and cardiac abnormalities such as arrhythmia, hypertrophic cardiomyopathy and myocardial infarction can be diagnosed.

Electrocardiogram is the most convenient tool for diagnosing myocardial infarction. Current guidelines suggest that mortality rate can be reduced significantly if patients diagnosed with myocardial infarction receive reperfusion therapy in cardiac catheterization room within 90 minutes after first medical contact, and therefore electrocardiogram is valuable in clinical treatment of acute myocardial infarction. However, diagnosis of acute myocardial infarction requires 12-lead electrocardiogram because only 12-lead electrocardiogram is able to detect the abnormal electrical activities of the heart caused by myocardial infarction, through which the extent of blockage of the coronary artery can be determined.

Blood is supplied to the heart by three coronary arteries, which are right coronary artery (RCA), left anterior descending artery (LAD) and left circumflex artery (LCX) respectively. Blockage of different arteries requires different medical treatments, and the prognoses also differ therefrom.

The interpretation of an electrocardiography involves observing the changes of rising and falling waveforms of ST segment in each electrocardiogram lead. However, multiple electrocardiogram leads in the same group of electrocardiogram need to be considered before making a diagnosis since measurement from one lead does not provide sufficient information. Said same group includes anterior leads V1 to V6, inferior leads II, III, aVF, and lateral/apical leads I, aVL, V5, V6. These electrocardiogram leads in the same group also represent the anatomical location of the outer layer of myocardium. Anomalies in the anterior leads are often due to blockage of the left anterior descending artery. Anomalies in the inferior leads are often due to blockage of the right coronary artery. Anomalies in the lateral/apical leads are often due to blockage of the left circumflex artery. Therefore, only a complete 12-lead electrocardiography can be used to accurately diagnose the acute myocardial infarction.

Conventional electrocardiogram devices can be classified into the following two types:

First, professional electrocardiogram device: ten electrode patches are attached to specific positions located on the patient's limbs and on the surface of the chest. By attaching the electrode patches onto different portions of a human body, the professional electrocardiogram device can measure 12 electrocardiogram leads (e.g. recording the electrical activities of the heart beat from 12 different directions, and therefore 12 vector readings can be obtained) can be measured simultaneously, from which working condition of different heart tissues can be analyzed, and a thorough diagnosis of heart condition can be made.

However, the cost of a professional electrocardiogram is too much for ordinary users, and meanwhile, professional electrocardiograms are not portable due to their size and weight.

Second, watch-style electrocardiogram device: in order to overcome the shortcomings of professional electrocardiograms and allow non-professional users, especially patients with cardiac arrhythmia, to perform electrocardiogram test timely when feeling ill, a wearable watch-style electrocardiogram device has been developed. The watch-style electrocardiogram device has two metal contacts. One metal contact is located in the back of the watch, and the other is located on the edge. To perform an electrocardiogram test, the user simply has to wear the device on one wrist, and touch the metal contact on the edge with the other hand.

However, the watch-style electrocardiogram device only has two metal contacts, and has to be worn on the wrist when performing the electrocardiogram test, and therefore, the watch-style electrocardiogram device measures and records the electrical activities of the heart beat from one direction only, and only one vector reading can be obtained, which means only one electrocardiogram lead is measured. The insufficiency of the vector readings means the watch-style electrocardiogram device cannot be used for detecting potentially lethal myocardial ischemia such as acute myocardial infarction, and can only be used for heart rate monitoring or cardiac arrhythmia detection. Currently there is no portable electrocardiogram device for a patient with history of myocardial infarction to detect whether the patient is suffering from myocardial ischemia, and therefore no alarm can be raised, and the patient cannot seek medical attention early.

To overcome the shortcomings, the present invention provides a portable multi-lead electrocardiogram device to mitigate or obviate the aforementioned problems.

SUMMARY OF THE INVENTION

The main objective of the present invention is to provide a portable multi-lead electrocardiogram device that does not sacrifice detecting capability for portability. In addition to detecting cardiac arrhythmia, the device can further detect acute myocardial infarction and other myocardial ischemia related diseases, which cannot be detected by using a watch-style single lead electrocardiogram.

The portable multi-lead electrocardiogram device has a holding case, a signal processing module, three metal contacts, a body contact direction, and a transverse direction perpendicular to each other. The signal processing module is located in the holding case. The three metal contacts are located on an exterior surface of the holding case and are electrically connected to the signal processing module. The three metal contacts are respectively a body contact, a left hand contact and a right hand contact. The left hand contact is for contacting a finger or a palm of a left hand. The left hand contact has a left hand contact plane. The right hand contact is for contacting a finger or a palm of a right hand. The right hand contact has a right hand contact plane. The body contact direction and the transverse direction are perpendicular to each other. The left hand contact and the right hand contact are located on a top of the holding case.

The left hand contact plane and the right hand contact plane are inclined respectively toward opposite sides along the transverse direction.

The advantage of the present invention is that the three metal contacts are located on the exterior surface of the holding case. One of the metal contact can be used for reference while the other two metal contacts can measure the electrical activities of the heart beat from two different directions simultaneously. The electrical signal generated by the heart beat is a three dimension vector. A watch-style electrocardiogram device can only measure from one single direction, and therefore loses a lot of vector information. The present invention is able to measure from two different directions simultaneously, and therefore can preserve more vector information, thereby greatly improving detecting accuracy.

Besides, a 12-lead electrocardiogram same as a professional electrocardiogram device can be performed by the present invention by combining the measuring results from different body portions. To be precise, to perform a 12-lead electrocardiogram, the user holds the present invention with both hands, and abuts one of the metal contacts against designated positions on lower limbs and chest while keeping the thumbs in contact with the other two metal contacts respectively. Combined with improved accuracy and the ability to perform full 12-lead electrocardiogram, the present invention not only detects cardiac arrhythmia, which is the only function of a conventional watch-style electrocardiogram, but also detects acute myocardial infarction and other myocardial ischemia related diseases, which cannot be detected by using a conventional watch-style single lead electrocardiogram. Meanwhile, by having less metal contacts, the present invention is more compact and light-weighted, which makes the device portable and allows the user to perform electrocardiogram test timely when feeling ill.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
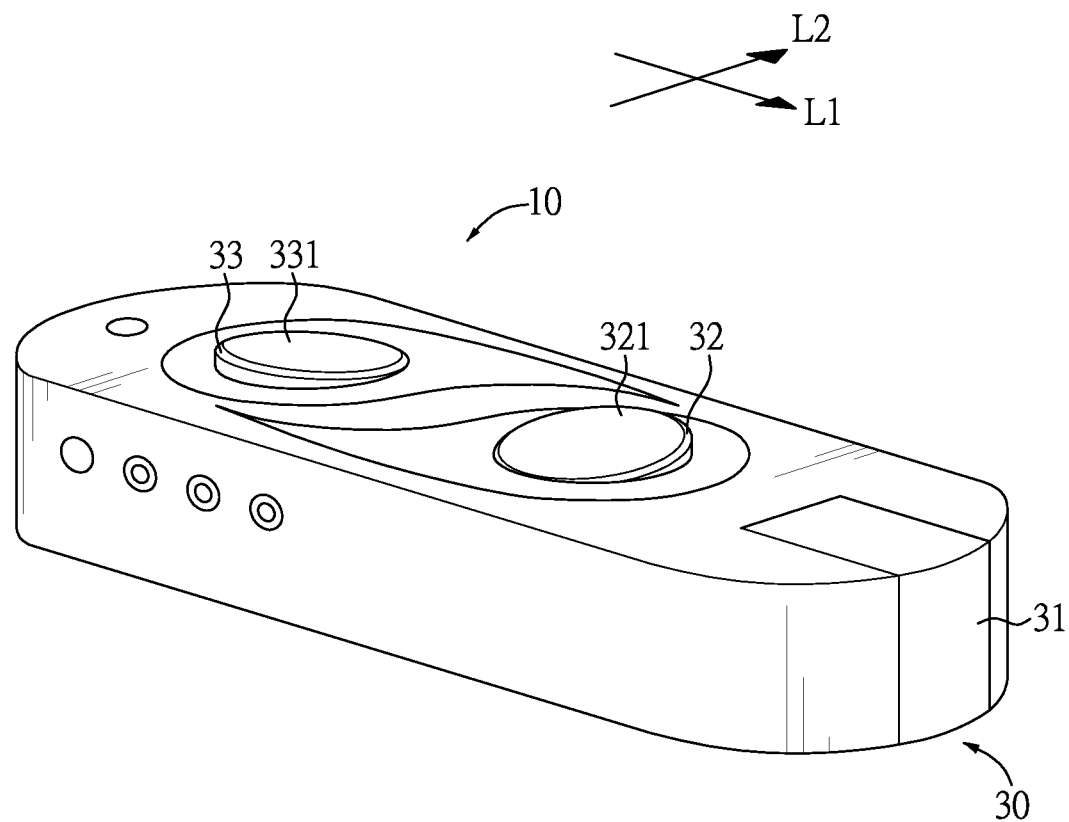
FIG. 1 is a perspective view of a portable multi-lead electrocardiogram device in accordance with the present invention.
Figure 2:
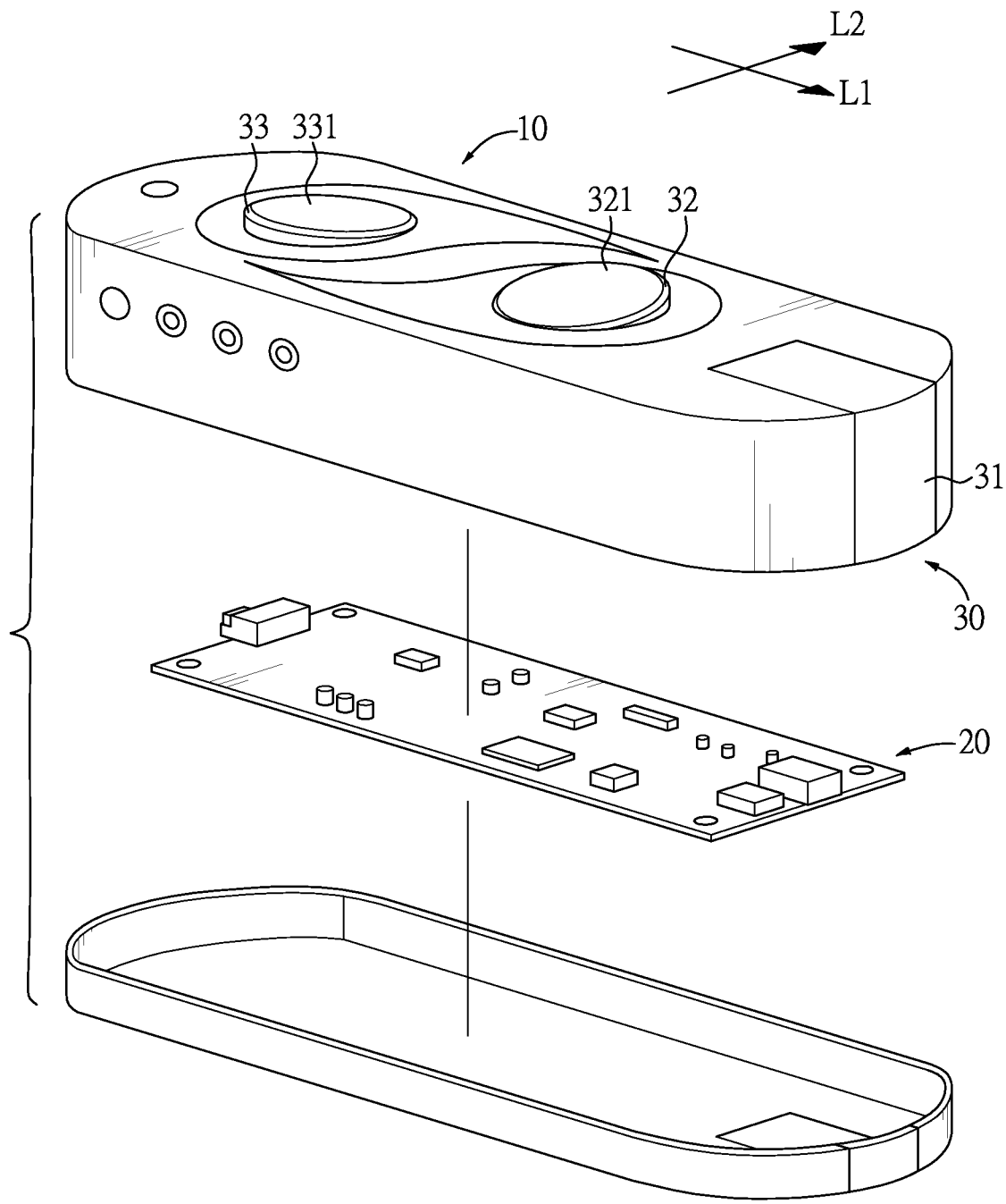
FIG. 2 is an exploded view of the portable multi-lead electrocardiogram device in FIG. 1.

With reference to FIGS. 1 and 2, a portable multi-lead electrocardiogram device in accordance with the present invention comprises a holding case 10, a signal processing module 20 and three metal contacts 30.

The holding case 10 is for a user to hold with one or two hands. In a preferred embodiment, the holding case 10 is an elongated case extending along a body contact direction L1. However, the holding case 10 can be in any other shape as long as it can be held with one or two hands by the user.

The signal processing module 20 is located in the holding case 10.

The metal contacts 30 are located on an exterior surface of the holding case 10 and electrically connected to the signal processing module 20. The metal contacts 30 are respectively a body contact 31, a left hand contact 32 and a right hand contact 33. The left hand contact 32 is for contacting a finger or palm of a left hand, and the right hand contact 33 is for contacting a finger or palm of a right hand.

In a preferred embodiment, the body contact 31 is located on a side of the holding case 10 that is toward the body contact direction L1. The left hand contact 32 and right hand contact 33 are located on a top of the holding case 10, and the three metal contacts 30 are arranged along the body contact direction L1. A left hand contact plane 321 is formed on a top of the left hand contact 32, and a right hand contact plane 331 is formed on a top of the right hand contact 33. A transverse direction L2 is perpendicular to the body contact direction L1. The left hand contact plane 321 and the right hand contact plane 331 are inclined respectively toward opposite sides along the transverse direction L2.

By arranging the three metal contacts 30 along the body contact direction L1 and making the left hand contact plane 321 and the right hand contact plane 331 inclined toward opposite sides, when the user holds the holding case 10 and abuts the body contact 31 against the body of the user, the slopes of the left hand contact plane 321 and the right hand contact plane 331 guide the user to put thumbs on the corresponding contact planes respectively. However, the shape of the holding case 10 and the location of the three metal contacts 30 are not limited by the aforementioned, as long as the user can be guided to touch the left hand contact 32 with the finger or the palm of the left hand, and touch the right hand contact 33 with the finger or the palm of the right hand when the body contact 31 of the holding case 10 faces toward the user. For example, the left hand contact 32 and the right hand contact 33 can be located on two opposite ends along the extending direction of the elongated holding case 10, while the body contact 31 protrudes from a side of the holding case 10.

Figure 3:
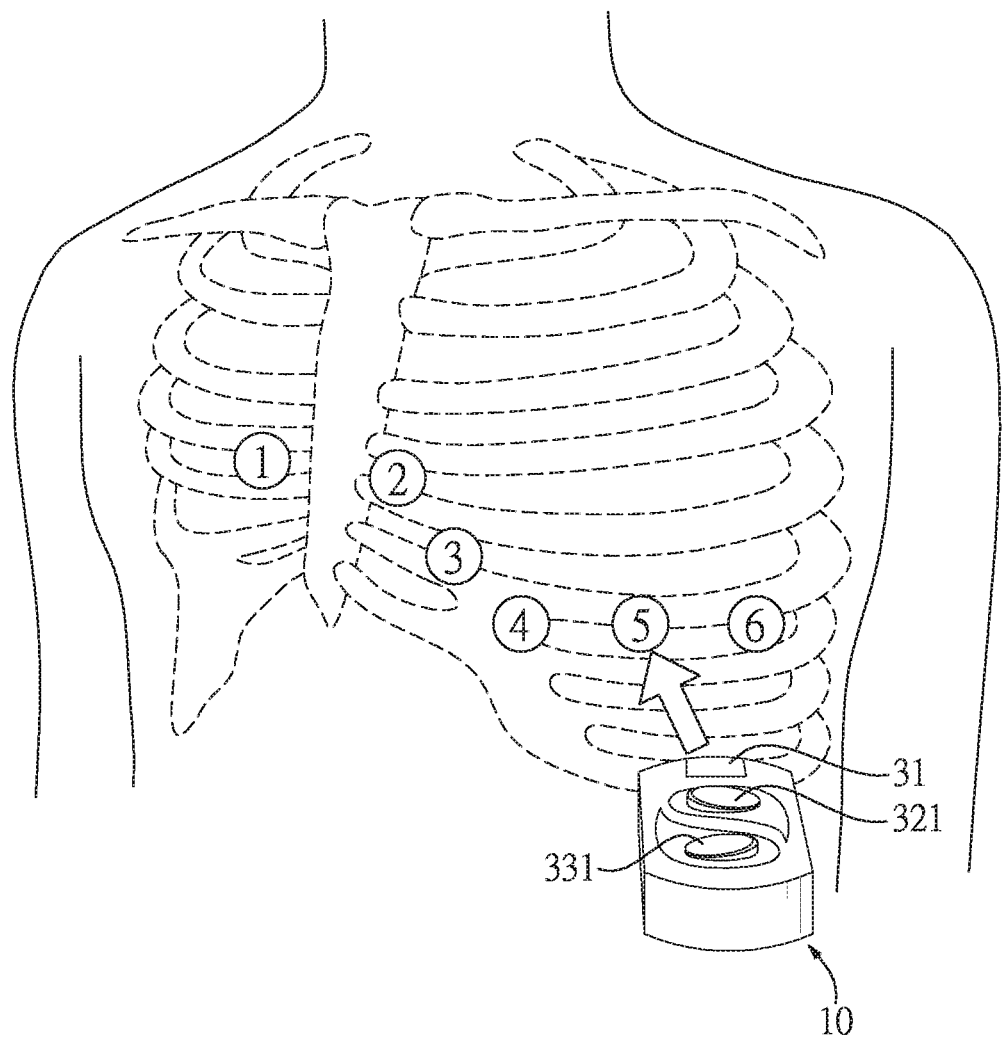
FIGS. 3 to 5 are perspective views of the portable multi-lead electrocardiogram device in FIG. 1, showing different operating statuses of the present invention.
Figure 4:
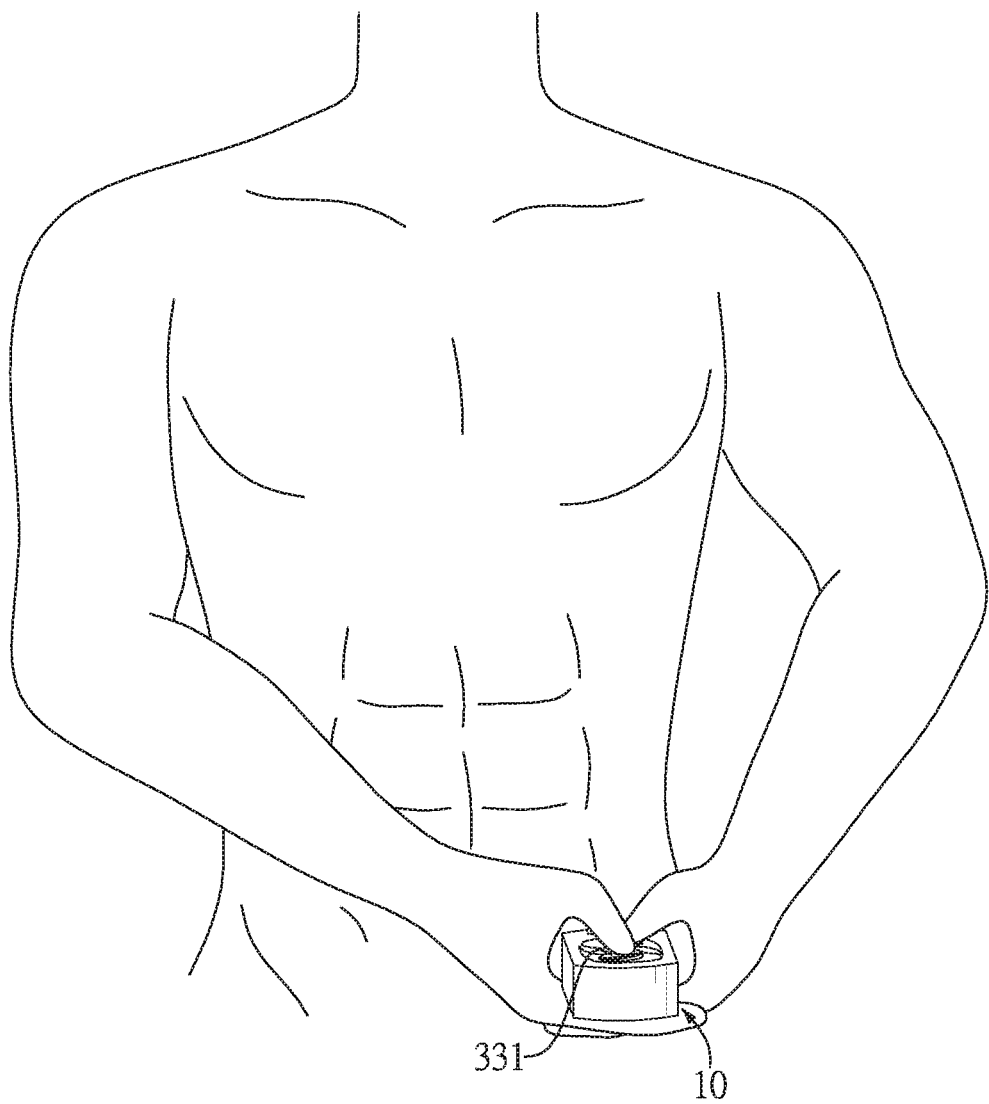

With reference to FIGS. 3 and 4, to use the present invention, the user holds the holding case 10 with both hands with the body contact 31 facing towards the body of the user. The user puts his left thumb and right thumb on the left hand contact plane 321 and the right hand contact plane 331 respectively.

Figure 5:
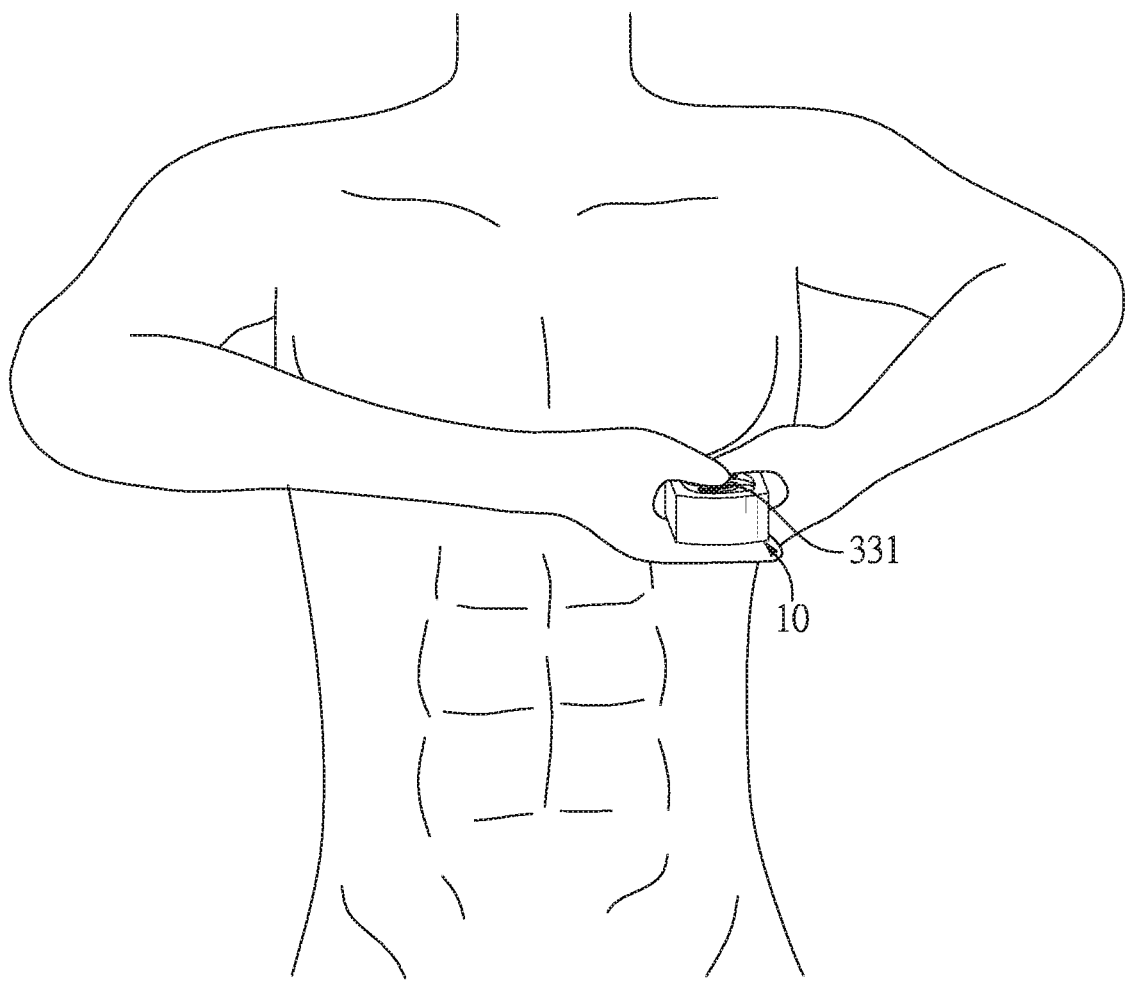

With reference to FIGS. 3 and 5, the user then abuts the body contact 31 sequentially against six designated positions located on the chest while keeping the thumbs in contact with the metal contacts 30 to measure and record six chest leads. With information of the six chest leads, the heart is fully observed in the horizontal plane. The user then continues to abut the body contact 31 against other portions on the body to finish measuring and recording complete 12 electrocardiogram leads.

Figure 6:
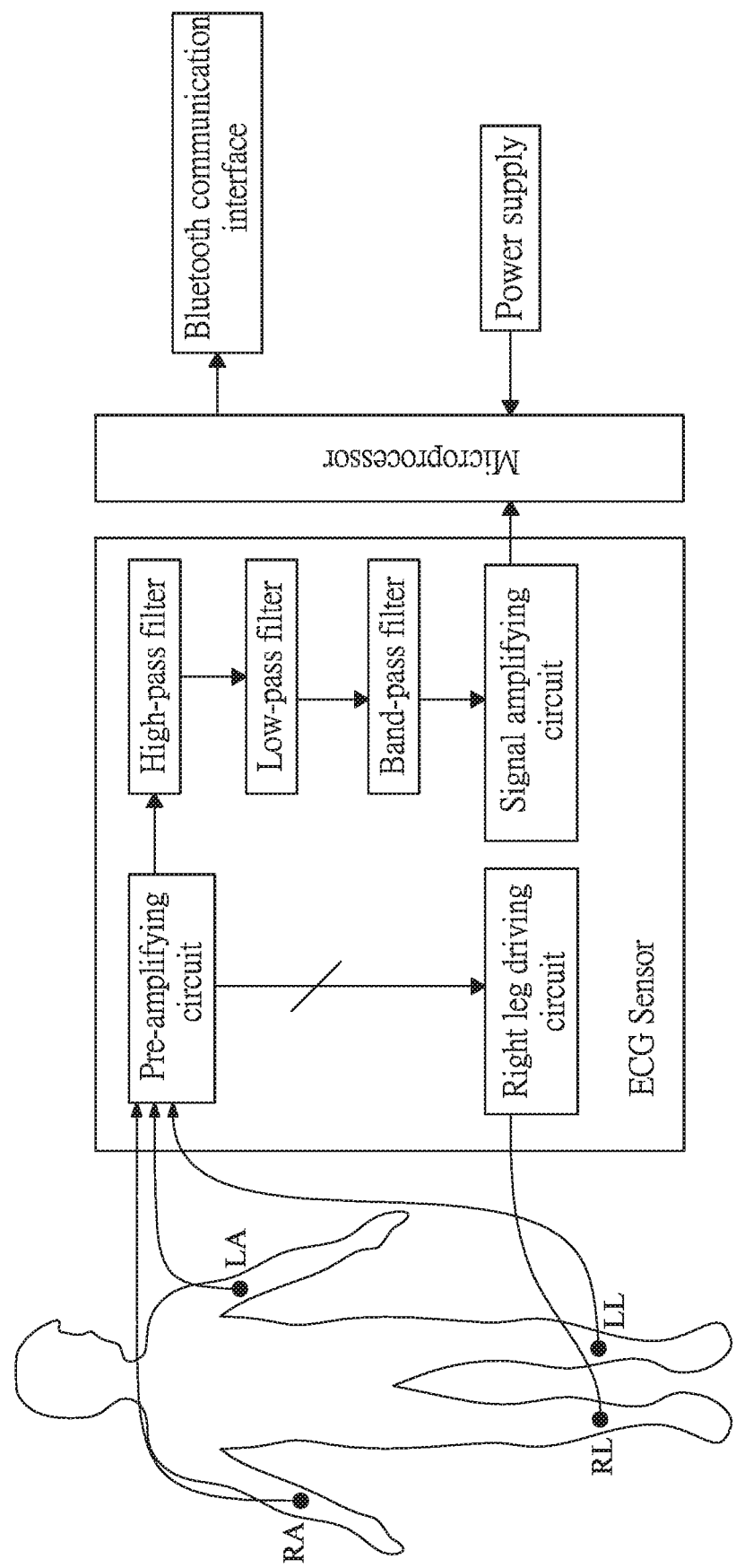
FIG. 6 is a block diagram of the portable multi-lead electrocardiogram device in FIG. 1, showing the electronic design of a signal processing module in the portable multi-lead electrocardiogram device.

With reference to FIG. 6, the signal processing module 20 comprises amplifying circuits, a driving circuit, filters and a microprocessor, and can further communicate with other electronic devices through Bluetooth.

In summary, by developing a portable multi-lead electrocardiogram device with three metal contacts, the present invention is portable and allows the user to perform electrocardiogram test timely when feeling ill.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A portable multi-lead electrocardiogram device comprising:
    a holding case;
    a signal processing module located in the holding case;
    three metal contacts located on an exterior surface of the holding case and electrically connected to the signal processing module; the three metal contacts respectively being
        a body contact;
        a left hand contact for contacting a finger or a palm of a left hand; the left hand contact having a left hand contact plane; and
        a right hand contact for contacting a finger or a palm of a right hand; the right hand contact having a right hand contact plane; and
    wherein the portable multi-lead electrocardiogram device has a body contact direction and a transverse direction perpendicular to each other;
    wherein the left hand contact and the right hand contact are located on a top of the holding case; the left hand contact plane and the right hand contact plane are inclined respectively toward opposite sides along the transverse direction.

2. The portable multi-lead electrocardiogram device as claimed in claim 1, wherein the body contact is located on a side of the holding case.

3. The portable multi-lead electrocardiogram device as claimed in claim 2, wherein
    the body contact is located on the holding case on the side that is toward the body contact direction.

4. The portable multi-lead electrocardiogram device as claimed in claim 3, wherein
    the holding case extends along the body contact direction; and
    the metal contacts are arranged along the body contact direction.

5. The portable multi-lead electrocardiogram device as claimed in claim 4, wherein
    the left hand contact is for contacting a thumb of the left hand; and
    the right hand contact is for contacting a thumb of the right hand.

6. The portable multi-lead electrocardiogram device as claimed in claim 1, wherein
    the holding case extends along the body contact direction; and
    the metal contacts are arranged along the body contact direction.

7. The portable multi-lead electrocardiogram device as claimed in claim 1, wherein
    the left hand contact is for contacting a thumb of the left hand; and
    the right hand contact is for contacting a thumb of the right hand.

* * * * *